United States Patent
Frank et al.

(10) Patent No.: US 7,868,295 B2
(45) Date of Patent: Jan. 11, 2011

(54) ADVANCED CALORIMETRIC SPECTROSCOPY FOR COMMERCIAL APPLICATIONS OF CHEMICAL AND BIOLOGICAL SENSORS

(75) Inventors: David L. Frank, Boca Raton, FL (US); Rodney L. Clark, Gurley, AL (US)

(73) Assignee: Innovative American Technology, Inc., Boca Raton, FL (US)

( * ) Notice: Subject to any disclaimer, the term of this patent is extended or adjusted under 35 U.S.C. 154(b) by 565 days.

(21) Appl. No.: 11/969,889

(22) Filed: Jan. 5, 2008

(65) Prior Publication Data

US 2010/0282969 A1 Nov. 11, 2010

(51) Int. Cl.
*G01N 21/84* (2006.01)
(52) U.S. Cl. .................................. 250/339.07
(58) Field of Classification Search ................ 250/330, 250/332, 338.1, 339.07, 352, 370.01, 370.08; 73/24.02
See application file for complete search history.

(56) References Cited

U.S. PATENT DOCUMENTS

| | | | |
|---|---|---|---|
| 4,158,773 A | 6/1979 | Novak | |
| 4,799,828 A | 1/1989 | Georgii | |
| 5,056,958 A | 10/1991 | Campbell | |
| 5,241,573 A | 8/1993 | Thacker | |
| 5,633,508 A | 5/1997 | Schleppenbach | |
| 5,665,970 A | 9/1997 | Kronenberg et al. | |
| 5,719,324 A | 2/1998 | Thundat et al. | |
| 5,737,086 A * | 4/1998 | Gerber et al. | 356/432 |
| 5,838,759 A | 11/1998 | Armistead | |
| 5,923,421 A | 7/1999 | Rajic et al. | |
| 6,080,988 A * | 6/2000 | Ishizuya et al. | 250/338.1 |

(Continued)

FOREIGN PATENT DOCUMENTS

JP 10197464 7/1998

(Continued)

OTHER PUBLICATIONS

International Search Report dated Jun. 12, 2008 for PCT/US2008/050332.

(Continued)

*Primary Examiner*—David P Porta
*Assistant Examiner*—Marcus H Taningco
(74) *Attorney, Agent, or Firm*—Jose Gutman; Fleit Gibbons Gutman Bongini & Bianco PL (57) ABSTRACT

A chemical and biological sensor system (200) includes at least one micro-cantilever sensing element (202) and a mechanism for collecting aerosol, liquid, and solid particles, and depositing the particles as a film layer (146) on a stack (140) formed with the cantilever. The deposited particles include chemical or biological species to be analyzed. A polarized light (242) illuminates the stack (140) at a grazing incidence angle to a specific wavelength of light. The light is polarized in a plane parallel to the stack (140). The polarized light (242) heats the cantilever with different wavelengths of the light spectrum. Readout electronics detect movement of the cantilever (202) as a result of heat transfer from the light and provide spectral data signals corresponding to the detected movement. A spectral analyzer (840) analyzes the spectral data signals, compares spectral images of the materials present to spectral images of known materials, and identifies one or more chemical or biological species present.

20 Claims, 9 Drawing Sheets

U.S. PATENT DOCUMENTS

| | | | |
|---|---|---|---|
| 6,212,939 | B1 | 4/2001 | Thundat |
| 6,289,717 | B1 | 9/2001 | Thundat et al. |
| 6,370,222 | B1 | 4/2002 | Cornick |
| 6,433,335 | B1 | 8/2002 | Kronenberg et al. |
| 6,479,826 | B1 | 11/2002 | Klann et al. |
| 6,545,281 | B1 | 4/2003 | McGregor et al. |
| 6,845,873 | B1 | 1/2005 | Chattey |
| 6,891,470 | B2 | 5/2005 | Bohinc |
| 6,937,692 | B2 | 8/2005 | Johnson |
| 6,980,483 | B2 | 12/2005 | McDonald |
| 6,998,617 | B2 | 2/2006 | D'Emilio et al. |
| 7,026,944 | B2 | 4/2006 | Alioto et al. |
| 7,030,755 | B2 | 4/2006 | Bohinc |
| 7,064,336 | B2 | 6/2006 | Archer et al. |
| 7,105,358 | B2 * | 9/2006 | Majumdar et al. .......... 436/518 |
| 7,116,235 | B2 | 10/2006 | Alioto et al. |
| 7,141,385 | B2 * | 11/2006 | Bottomley et al. ........... 435/7.4 |
| 7,151,447 | B1 | 12/2006 | Willms et al. |
| 7,183,554 | B2 | 2/2007 | Gallagher et al. |
| 7,356,115 | B2 | 4/2008 | Ford et al. |
| 2002/0175291 | A1 | 11/2002 | Reeder et al. |
| 2003/0108150 | A1 | 6/2003 | Franke |
| 2003/0144800 | A1 | 7/2003 | Davis et al. |
| 2003/0165211 | A1 | 9/2003 | Lee et al. |
| 2003/0201394 | A1 | 10/2003 | Peoples |
| 2004/0018060 | A1 | 1/2004 | Knezek et al. |
| 2004/0119591 | A1 | 6/2004 | Peeters |
| 2004/0126895 | A1 | 7/2004 | Overbeck et al. |
| 2004/0148137 | A1 | 7/2004 | Zerwekh et al. |
| 2005/0011849 | A1 | 1/2005 | Chattey |
| 2005/0023477 | A1 | 2/2005 | Archer et al. |
| 2005/0082485 | A1 | 4/2005 | Tatsuo |
| 2005/0156734 | A1 | 7/2005 | Zerwekh et al. |
| 2005/0205793 | A1 | 9/2005 | Bohinc |
| 2005/0220247 | A1 | 10/2005 | Ruddy et al. |
| 2005/0258372 | A1 | 11/2005 | McGregor et al. |
| 2005/0275545 | A1 | 12/2005 | Alioto et al. |
| 2006/0097171 | A1 | 5/2006 | Balchunas et al. |
| 2006/0138331 | A1 | 6/2006 | Guillebaud et al. |
| 2006/0284094 | A1 | 12/2006 | Inbar |
| 2007/0001123 | A1 | 1/2007 | Andrews et al. |

FOREIGN PATENT DOCUMENTS

| | | |
|---|---|---|
| KR | 10-1992-7004134 | 12/1992 |
| KR | 10-1005-0067392 | 7/2005 |
| WO | WO98-00681 | 1/1998 |
| WO | WO2006-085999 | 8/2006 |

OTHER PUBLICATIONS

U.S. Appl. No. 11,291,574, filed Dec. 2005, Frank.
U.S. Appl. No. 11,363,594, filed Feb. 2006, Frank.
U.S. Appl. No. 11,564,193, filed Nov. 2006, Frank.
U.S. Appl. No. 11,931,370, filed Oct. 2007, Frank.
International Preliminary Report on Patentabiilty for PCT/US06/46255 mailed Sep. 24, 2008.
International Search Report and Written Opinion of the International Searching Authority for PCT/US06/46255 mailed Sep. 25, 2007.
Written Opinion of the International Searching Authority for PCT/US07/085578 dated Jan. 23, 2009.
International Search Report for PCT/US07/085578 dated Jan. 23, 2009.
PCT Application No. PCT/US2007/085578 filed Nov. 27, 2007.
PCT Application No. PCT/US2006/46255 filed Nov. 30, 2006.
Non-Final Rejection for U.S. Appl. No. 11/291,574 dated Dec. 2, 2008.
Final Rejection for U.S. Appl. No. 11/291,574 dated Mar. 20, 2008.
Notice of Allowance for U.S. Appl. No. 11/291,574 dated May 20, 2009.
Non-Final Rejection for U.S. Appl. No. 11/363,594 dated Aug. 23, 2006.
Notice of Allowance for U.S. Appl. No. 11/363,594 dated Sep. 27, 2006.
Non-Final Rejection for U.S. Appl. No. 11/564,183 dated Jun. 25, 2009.
Non-Final Rejection for U.S. Appl. No. 11/931,370 dated Dec. 12, 2008.
Final Rejection for U.S. Appl. No. 11/931,370 dated Sep. 9, 2009.
Final Rejection for U.S. Appl. No. 11/564,193 dated Jan. 8, 2010.
Notice of Allowance for U.S. Appl. No. 11/930,229 dated Apr. 7, 2010.
International Search Report and Written Opinion for PCT/US09/050299 dated Mar. 3, 2010.
Notice of Allowance for U.S. Appl. No. 11/931,370 dated Mar. 30, 2010.
International Search Report for PCT/US09/038064 dated Jul. 31, 2009.
International Search Report and Written Opinion for PCT/US09/044486 dated Dec. 23, 2009.
International Search Report and Written Opinion for PCT/US09/044475 dated Jan. 6, 2010.
International Search Report and Written Opinion for PCT/US09/045268 dated Jan. 29, 2010.
International Search Report and Written Opinion for PCT/US09/044494 dated Jan. 18, 2010.
Non-Final Rejection for U.S. Appl. No. 11/931,211 dated Apr. 30, 2010.

* cited by examiner

ADVANCED CALORIMETRIC SPECTROSCOPY FOR COMMERCIAL APPLICATIONS OF CHEMICAL AND BIOLOGICAL SENSORS

FIELD OF THE INVENTION

The present invention generally relates to the field of calorimetric spectroscopy, and more particularly relates to an advanced design for thermal detectors having miniature chemical and biological sensors for detecting minute amounts of chemical and biological materials in a consistent manner.

BACKGROUND OF THE INVENTION

Determining the presence and identity of unknown chemical species and/or biological species is challenging. Presently chemical and biological sensors that can detect the presence and identity of unknown chemical and biological analytes with enhanced sensitivity are either too large, too cumbersome, lack high selectivity and specificity, and are too costly for most commercial purposes. Calorimetric spectroscopy techniques have been developed in an attempt to address these issues. However the current calorimetric spectroscopy methods do not provide consistent spectra and do not support commercial applications for chemical and/or biological sensors.

The current calorimetric spectroscopy methods, such as those identified in U.S. Pat. No. 5,923,421, use a monochromator-illuminator beam path. The micro cantilever itself serves as the "exit slit" for the monochromator, causing only a narrow band of wavelengths to be imaged onto the cantilever. This narrow band IR light is focused upon the cantilever. The cantilever is coated with a thin film of sample material. According to the sample material's IR absorption properties it will absorb IR light at specific wavelengths. This absorbed energy will in turn heat up the cantilever. The cantilever is constructed of a bi-material sandwich. As a result of the heating the unequal thermal expansion in the bi-material cantilever causes the cantilever to bend in proportion to the absorbed power. The bending of the cantilever is monitored to identify the spectral image. This process results in excessive time frames for scanning as a result of the noise background and low signal-to-noise-ratio (SNR) of the system. The high noise background may also account for the inconsistencies between the expected IR spectra and existing calorimetric spectrometer spectra. The long scan times, inconsistent results, and inability to use established IR spectra information in support of a known material database, makes it difficult, if not impossible, to use current calorimetric spectrometer technologies in commercial applications for the detection and identification of chemical and/or biological materials.

Therefore a need exists to overcome the problems with the prior art as discussed above.

SUMMARY OF THE INVENTION

Briefly, in accordance with the present invention, a Micro-electro-mechanical (MEMS) micro cantilever, which has been coated with a thin film of sample material, is illuminated by a plane polarized IR light at grazing incidence to a specific wavelength. The absorbed energy will in turn heat up the cantilever. The cantilever is constructed of a bi-material sandwich. As a result of the heating the unequal thermal expansion in the bi-material cantilever causes the cantilever to bend in proportion to the absorbed power. The bending of the cantilever is monitored to identify one or more spectral images. Photothermal spectral data signals from readout electronics coupled to the micro cantilever represent at least one photothermal signature of sensed chemical or biological species. The use of plane polarized IR light results in rapid scan times, consistent results, and aligns with existing IR spectra database information enabling this technology to be applied as commercial devices for the detection and identification of chemical and biological materials.

In accordance with the inventive arrangements taught herein, a chemical and biological sensor capable of detection and identification of chemical and/or biological analytes that are present comprises a plane polarized IR light source and a thermal infrared detector array, for example, a micro bolometer, a thermopile, a pyroelectrics, or a micro cantilever. Such a chemical and/or biological sensor can detect the presence of minute amounts of chemical and/or biological analytes, for example less than parts per trillion (ppt), with increased selectivity by allowing a substantially simultaneous determination of the identity of the unknown species.

The micro cantilevers can be configured as a single test element, an array of micro cantilevers, or a two dimensional array of micro-cantilevers. The micro cantilevers optionally can comprise at least one of a thermal detector, a thermopile array, and a balometer array.

An advantage of the various embodiments of the present invention, as discussed above, is that it provides a novel approach to calorimetric spectroscopy that enables many commercial applications.

The present invention provides a low cost instrument for collecting IR spectra of chemical and biological specimens of nanogram to femtogram sample size. This is accomplished, according to one embodiment, by illumination of a micro-electro-mechanical (MEMS) micro-cantilever, which has been coated with a thin film of sample material, to plane polarized IR light at grazing incidence to illuminate the sample at a specific wavelength. The bending response of the micro-cantilever is measured optically as the IR source radiation is scanned through a range of IR wavelengths. This light source creates surface enhanced absorption in the sample film which significantly enhances the signal-to-noise-ratio (SNR) over that achieved by previous investigators.

Although surface enhanced absorption is commonly used in Fourier Transform Infrared (FTIR) absorption-reflection spectroscopy it has not been commonly applied to cantilever-based photo thermal spectroscopy. This novel invention makes the cantilever approach a viable method for constructing a compact spectrometer capable of consistent results from measuring nano-gram samples. Although this level of performance is approached with currently available FTIR absorption-reflection spectrometers, these devices are large and complex instruments, not easily adaptable to field use, and require long data collection times and larger sample sizes.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention. It is understood that the inventive arrangements are not limited to the precise arrangements and instrumentalities shown.

FIG. 3, represented by FIGS. 3A and 3B, is a diagram providing a calorimetric spectrometer response compared with IR photo spectra for two chemicals, i.e., 2-mercaptoethanol and TNT, illustrating inconsistent results obtained with a prior art system such as shown in FIG. 1;

FIG. 5, represented by FIGS. 5A and 5B, is a simple diagram illustrating absorption versus extinction coefficients;

FIG. 6, represented by FIGS. 6A and 6B, is a simple diagram illustrating deflection versus extinction coefficient;

FIG. 7, represented by FIGS. 7A and 7B, is a simple diagram illustrating a calculated cantilever deflection spectra for C—H bond in polyethylene as a function of incident angle and film thickness.

DETAILED DESCRIPTION

As required, detailed embodiments of the present invention are disclosed herein; however, it is to be understood that the disclosed embodiments are merely examples of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

The present invention applies a novel and advanced approach to calorimetric spectroscopy where, according to various embodiments, a Micro-electro-mechanical (MEMS) micro-cantilever, which has been coated with a thin film of sample material, is illuminated by a plane polarized IR light at grazing incidence to a specific wavelength. The absorbed energy will in turn heat up the cantilever. The cantilever is constructed of a bi-material sandwich. As a result of the heating the unequal thermal expansion in the bi-material cantilever causes the cantilever to bend in proportion to the absorbed power. The bending of one or more cantilevers is monitored to identify one or more spectral images. Photothermal spectral data signals from readout electronics coupled to the one or more cantilevers represent at least one photothermal signature of sensed chemical or biological species.

Figure 1A:
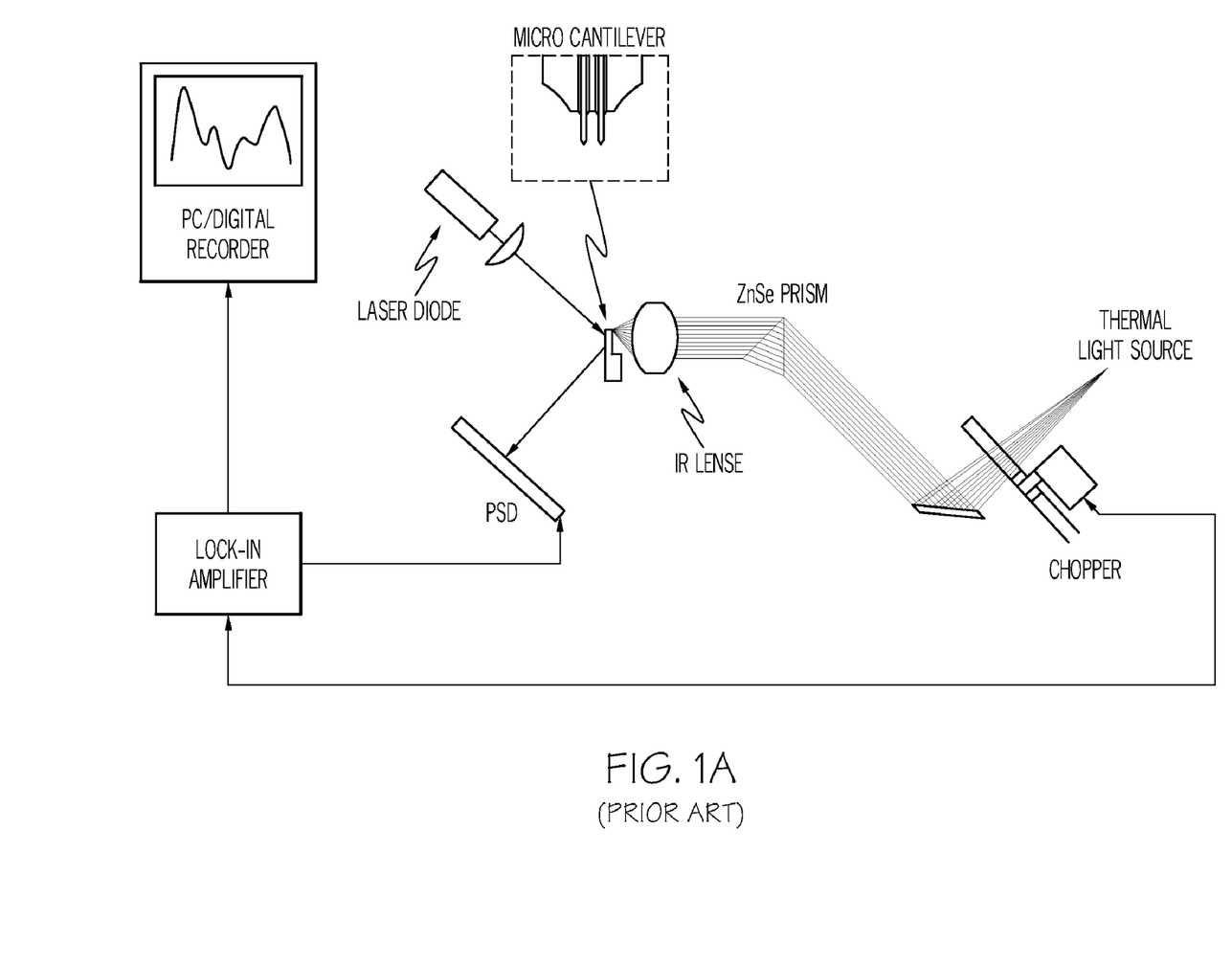
FIG. 1A is a diagrammatic representation of a prior art calorimetric spectrometer system used as a chemical detector in accordance with U.S. Pat. No. 5,923,421 which provides inconsistent results.
Figure 3A:
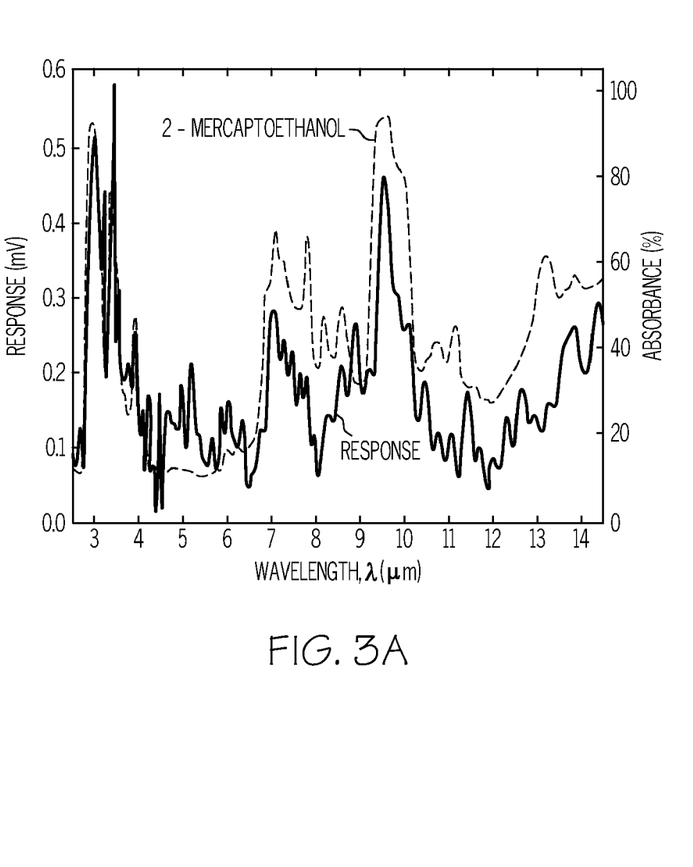
Figure 3B:
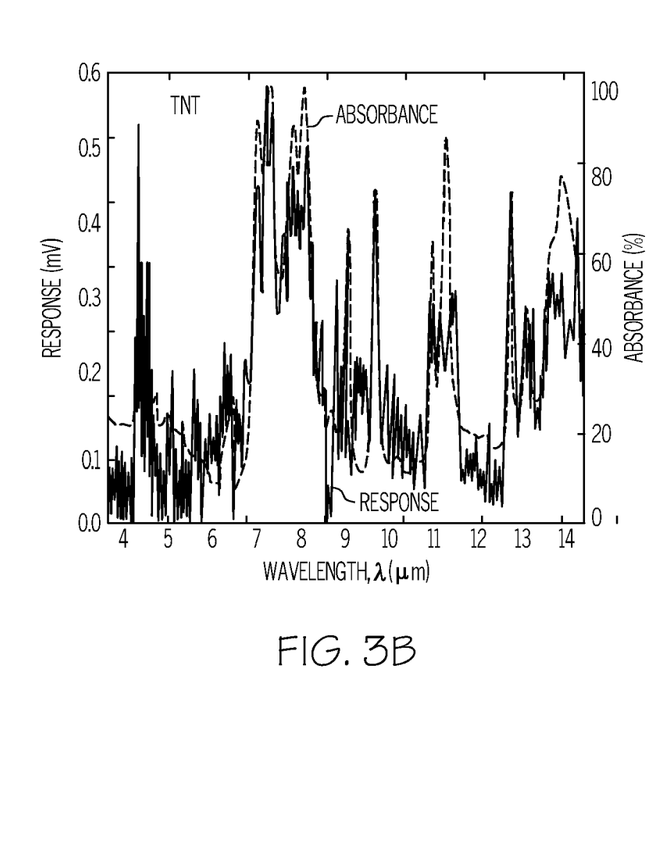

FIG. 1A provides a simple schematic diagram of an example of existing calorimetric spectrometer technologies, as represented by U.S. Pat. No. 5,923,421, results in excessive time frames for scanning due to the noise background and low signal to noise ratio (SNR) of this design. The high noise background may also account for inconsistencies between the expected IR spectra and existing calorimetric spectrometer spectra. For example, see FIG. 3 illustrating inconsistent results obtained with a prior art calorimetric spectroscopy system such as illustrated in FIG. 1A. A technical discussion of this response comparison with IR photo spectra is provided in the following publication: P. G. Datskos, S. Rajic, "Chemical detection based on absorption-induced and photo induced stresses in microelectromechanical system devices", J. Vac. Sci. Technol. B.19(4), July/August 2001.

The long scan times, inconsistent results, and inability to use established IR spectra information in support of a known material database, makes it difficult, if not impossible, to use current calorimetric spectrometer technologies in commercial applications for the detection and identification of chemical and biological materials.

With reference to FIG. 1, broadband IR light is generated using a thermal heat source, such as a nickchrome wire. The IR light from the hot wire is passed through a spinning shutter which chops the light on and off to form a pulsed light source. The IR light is then caused to pass through a ZnSe prism that separates out the various wavelengths of IR light. The wavelength of the light passed through the prism, and that makes it to the cantilever, is determined by the angle between the IR light source and the prism. The wavelengths can be scanned by rotation of the prism. The single wavelength selected by the prism is caused to pass through a focusing lens. This lens causes the IR light to be focused upon the cantilever.

The spot of light incident upon the cantilever is absorbed by the deposited sample film. This film having been deposited previously is composed of the material under test. The absorbed light at a particular wavelength causes the bimetallic cantilever to bend or deflect. The deflection of the cantilever is measured by readout electronics that include a read laser diode and a detector. The read laser diode produces a beam that is caused to reflect from the backside of the cantilever on to a quad or bicell optical light detector. This detector produces an electrical signal proportional to the cantilever deflection, which in turn is proportional to the absorption properties of the test sample at the wavelength of IR light. As the ZnSE prism is rotated the cantilever deflection is measured. This produces an absorption spectral response of the test sample film as a function of IR light wavelength. Different test materials have a unique spectral fingerprint (or photothermal signature) that can be used to identify the material under test. The time required to produce a spectral scan for this device is about 40 minutes. This long scan time is undesirable. The present invention proposes to reduce this scan time to approximately 1 minute or less.

Figure 2A:
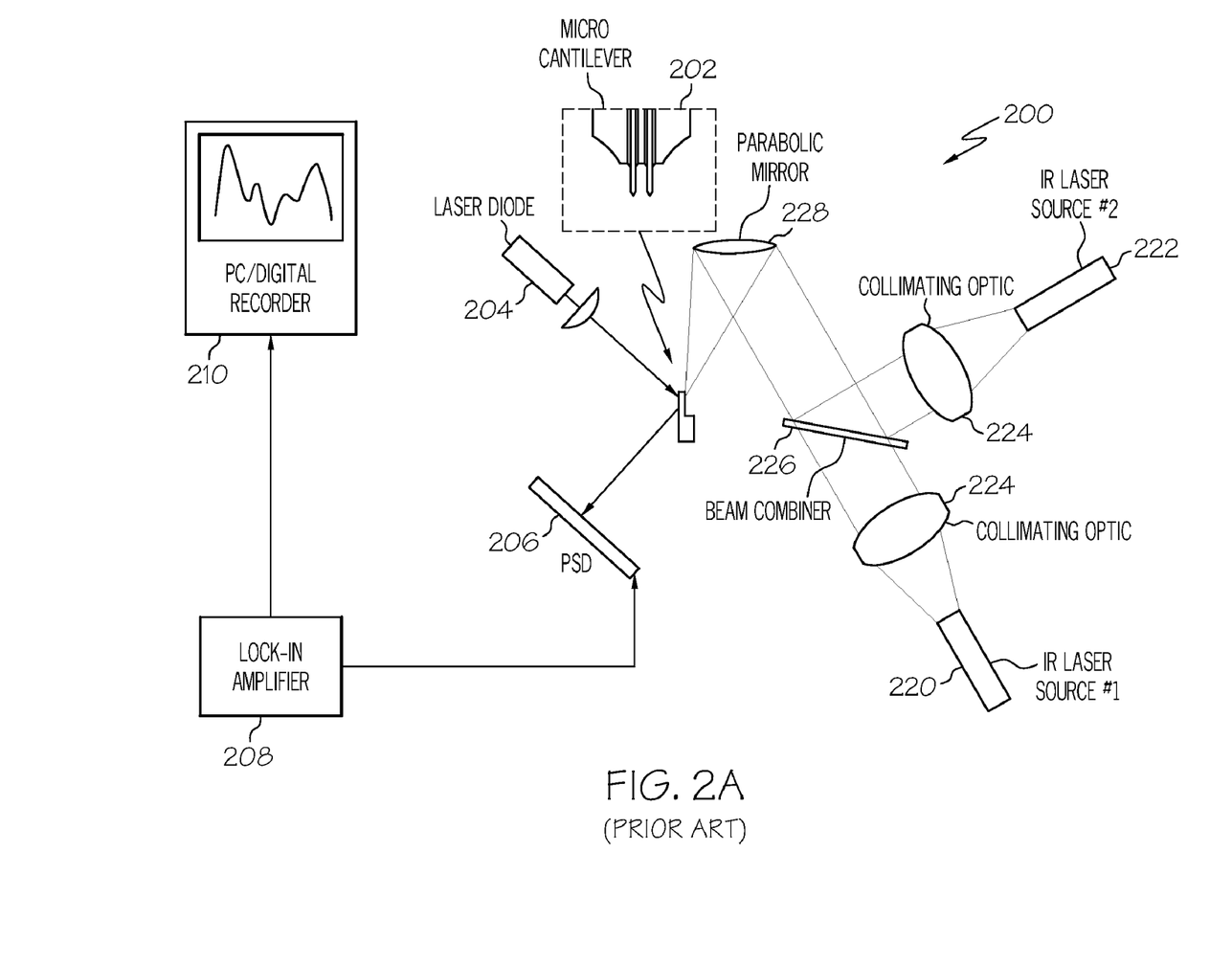
FIG. 2A is a diagrammatic representation of an advanced calorimetric spectrometer, according to one embodiment of the present invention, capable of use in commercial applications supporting chemical and biological sensors for field deployment.

FIG. 2A shows a simple schematic diagram of an example of an advanced calorimetric spectrometer system 200, according to one embodiment of the present invention. This system provides rapid time frames for scanning, high levels of sensitivity, consistent test results, and the expected IR spectra. This advanced design of a calorimetric spectrometer system 200, according to one embodiment, is based on the use of a plane polarized IR light at grazing incidence to a specific wavelength. It enables commercial applications for the detection and identification of chemical and biological materials.

The diagram of FIG. 2A shows a grazing incidence polarized IR light source comprising one or more laser sources 220, 222, with respective collimating optics 224, a beam combiner 226, and a parabolic mirror 228, to aim the plane polarized IR light at grazing incidence angle to at least one micro-cantilever 202. In this embodiment, multiple IR lasers 220, 222, each at a different IR wavelength, are used to generate polarized IR light. The light from each laser 220, 222, is expanded and collimated using the collimating lenses 224 as shown. The linearly polarized light from each laser is combined in the Beam Combiner 226. The resulting combined light beam is caused to reflect from the parabolic mirror 228. The parabolic mirror 228 causes the laser light to both focus and to strike the cantilever at a grazing incidence angle. By striking the cantilever at grazing incidence angle and by using light polarized in the plane of the surface of the at least one micro-cantilever 202 a larger absorption of the light occurs. This results in a greater heating effect in the test sample film, which was previously deposited upon a bimetallic surface of the micro-cantilever 202. Because the cantilever is bimetallic it bends upon heating. The bending of the cantilever is detected by readout electronics that, in this example, include a red laser diode 204 and a quad detector or bi-cell light detector 206. The red laser diode 204 generates a light beam that is caused to reflect off the opposite side of the cantilever 202 and strike a quad detector or bi-cell light detector 206. The detector 206 produces an electrical signal proportional to the cantilever bending. This invention produces a greater signal than previous cantilever detection devices by using plane polarized light in conjunction with grazing incidence. These two factors enhance absorption of IR light within the test sample.

Figure 1B:
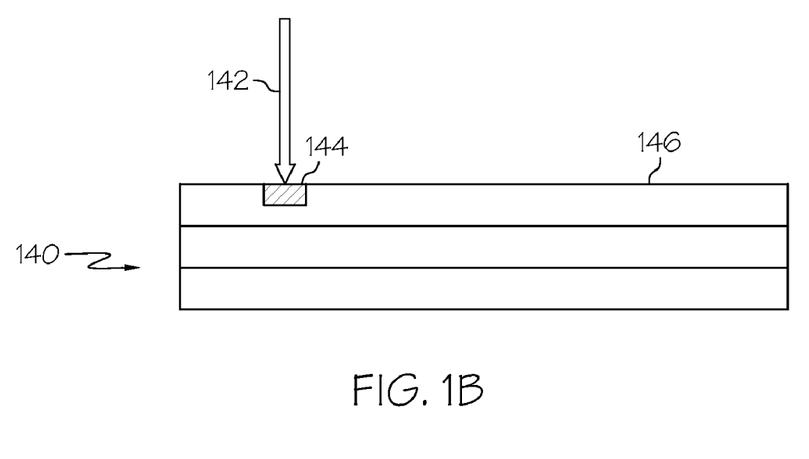
FIG. 1B is a diagrammatic representation of IR light rays illuminating a top film on a stack of a cantilever, according to the prior art system of FIG. 1A.
Figure 2B:
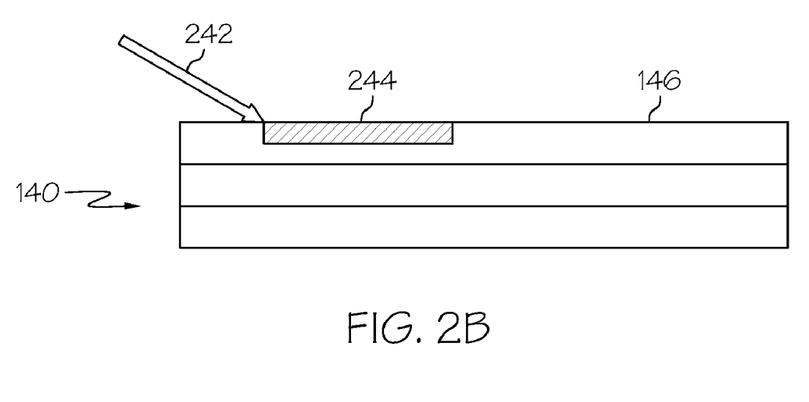
FIG. 2B is a diagrammatic representation of IR light rays illuminating a top film on a stack of a cantilever, according to the inventive system of FIG. 2A.

Both FIGS. 1B and 2B show the stack 140, formed by the micro-cantilever with the top layer film 146 on the stack 140, being illuminated with IR light. In FIG. 1B, the IR light 142 is delivered to the top film 146 in a direction that is normal (0 degrees) to the top surface of the top film 146. The IR light is arriving at a small spot 144 on the top film 146. The IR light is not collimated. In FIG. 2B, IR light is delivered to the top film 146 in a direction that is at a grazing angle (approximately >45 degrees and in various applications more preferably in a range of between approximately 70 degrees and 80 degrees) to the top surface of the top film 146. The IR light 242 is arriving at a large strip 244 on the top film 146. The IR light is collimated. As can be seen by comparing FIG. 1B to FIG. 2B, the IR light 242 at a grazing angle illuminates a larger strip cross-sectional area of the top surface of the top film 146 than the spot of IR light 142 at a normal angle of incidence. This transfers more energy from the IR light to the top film 146 and to the stack 140. Also, IR light polarized in the plane of the stack 140 transfers more light energy to the stack 140 than IR light that is not polarized. The combination of these two features of the present invention transfers more light energy and over a larger cross-sectional area of the stack 140, and thereby heats up the top film 146 and stack 140 faster and causing greater deflection movement of the cantilever. This improves the signal-to-noise-ration of the cantilever sensor element and makes the sensor measurement results more consistent than prior art systems.

In our laboratory testing and simulations, we concluded that the use of a plane polarized IR light at grazing incidence to a specific wavelength obtains the desired results. A plane polarized IR light as an illuminating source can be used for an advanced calorimetric spectrometer, according to one embodiment of the present invention. This results in rapid scan times, consistent test results, sensitivity at parts per trillion or greater (PPT), and aligns with expected IR spectra enabling this technology to be applied as commercial devices for the detection and identification of chemical and biological materials.

Figure 4:
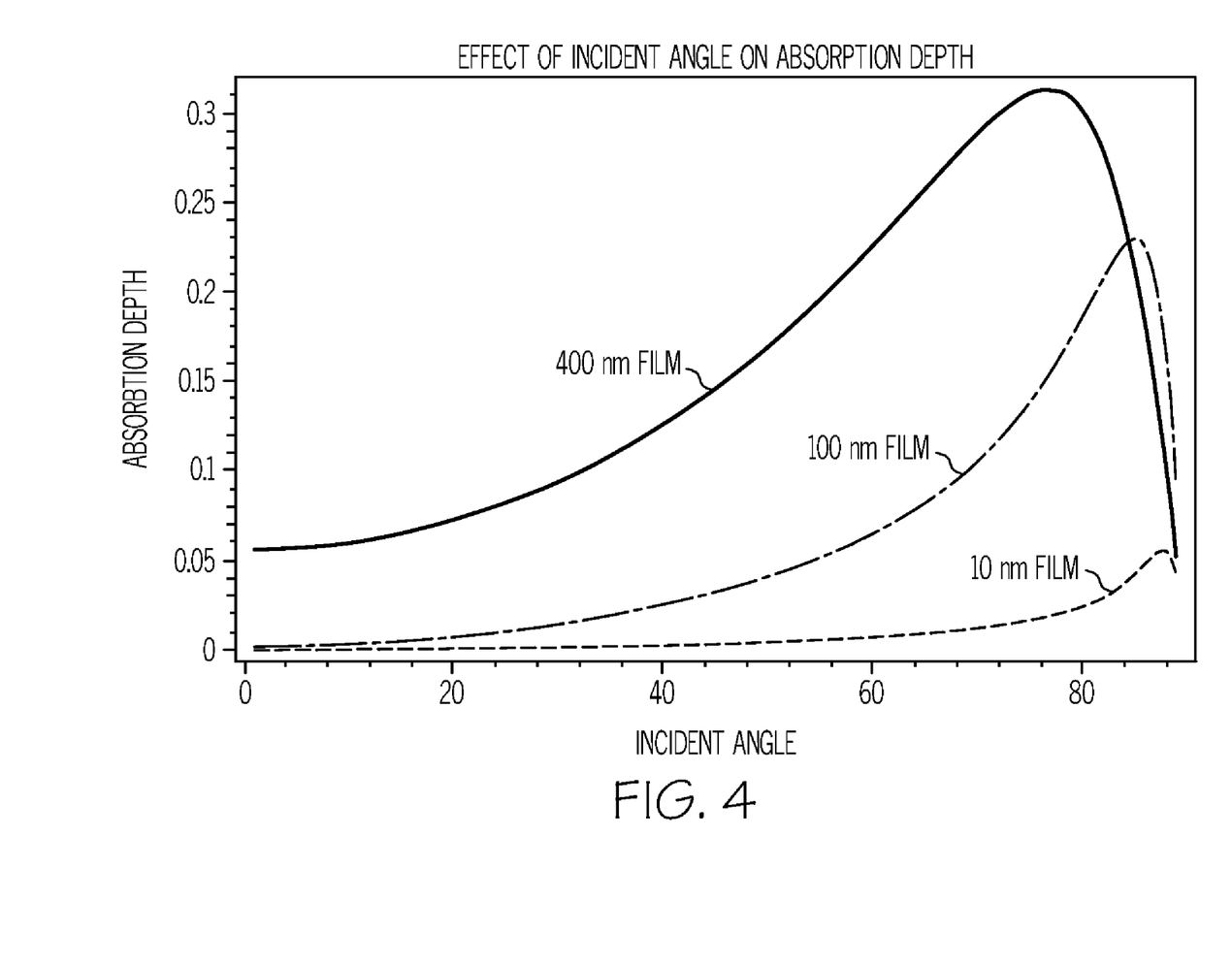
FIG. 4 is a simple diagram illustrating the Absorption Depth, i.e., (R0−R)/R0, versus incident angle of plane polarized light at wavelength 5 microns.

The sample under test comprises a thin layer of material that is deposited on a gold side of a bi-material cantilever. The thin layer can be deposited, for example, by adsorption. The resulting stack of materials, i.e., the thin layer of sample material and the two layers of material forming the cantilever, reflects and absorbs light as appropriate to its composition and the wavelength, polarization and incident angle of the IR light source. Using electromagnetic theory of thin film interference coatings the reflection properties can be calculated. FIG. 4 shows the calculated absorption strength or depth of the three layer composite thin film substrate structure as a function of incident angle for light polarized in the plane of the substrate. The absorption depth is defined as the difference between the surface reflectance of the film with an extinction coefficient of k=0.1 and of a film of similar thickness and refractive index with an extinction coefficient of k=0.0, divided by the reflectance of the former. The representative formula is shown below.

$$\text{Absorption Depth} = (R_0 - R)/R_0$$

As can be seen from FIG. 4, large incident angles produce a significant increase in the absorption depth for 10 nm, 100 nm, and 400 nm films. A prior art calorimetric spectrometer (CalSpec) system developed previously at ORNL, i.e., the Oak Ridge National Laboratory located in Tennessee, United States, was used with an unpolarized IR source at normal incident angle, i.e., at approximately 0 degrees incident angle. From FIG. 4 it can be seen that the thin film light absorption of the current normal incident angle CalSpec system could be significantly improved by using plane polarized IR light and at grazing incident angles, i.e., at approximately greater than around 45 degrees incident angles, and in various embodiments more preferably around approximately a range of near 70 to 80 degrees incident angles.

Figure 5A:
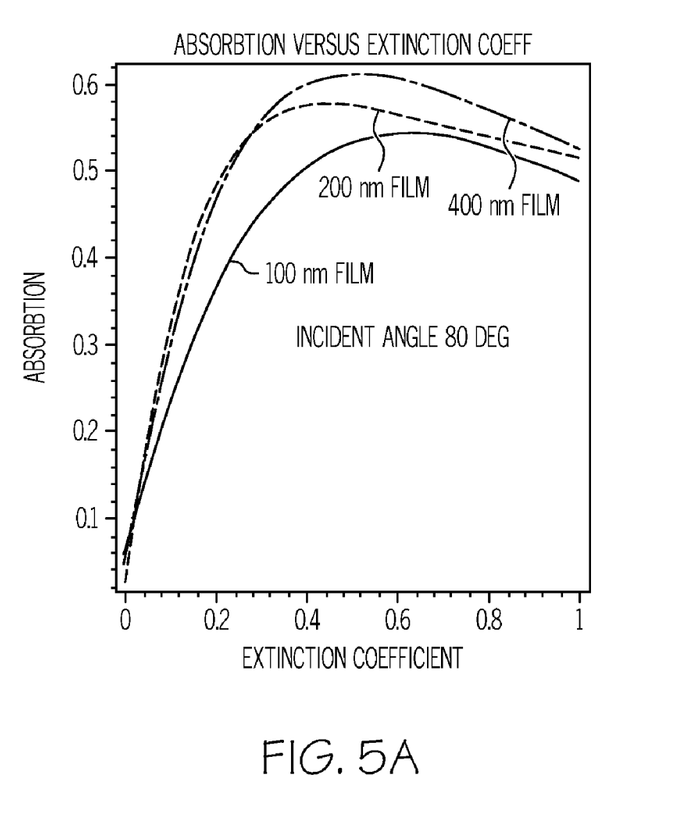
Figure 5B:
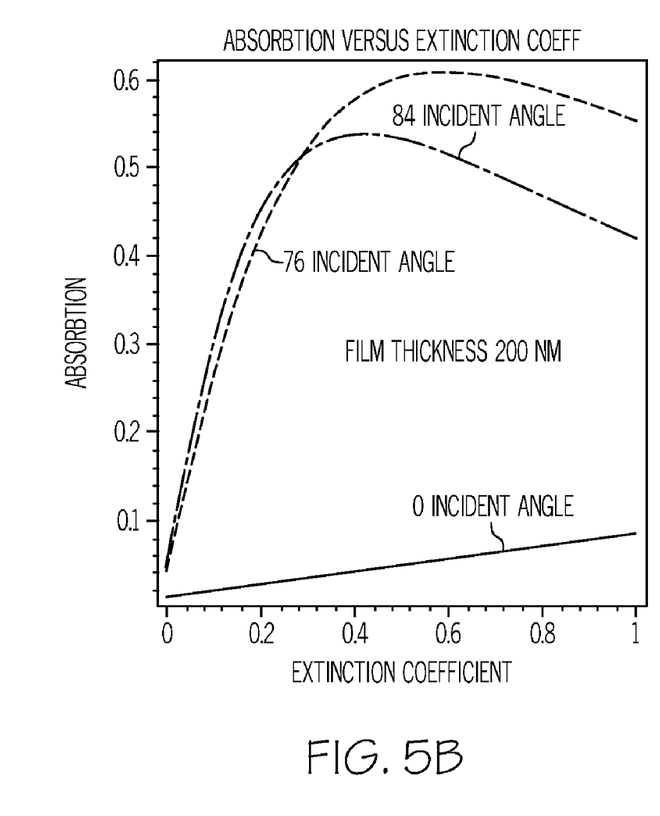

FIG. 5 presents calculated surface absorption coefficient versus the film extinction coefficient with refractive index, n=1.0. FIG. 5a shows calculated surface absorption versus extinction for three different film thicknesses at an incident angle of 80 degrees. FIG. 5b shows calculated surface absorption versus extinction for three different incident angles for a film thickness of 200 nm. Examination of these curves shows that for film thicknesses less than 200 nm and extinction coefficients less than k=0.20, the absorption coefficient is linear with extinction. For film thicknesses greater than 400 nm interference effects and absorption saturation effects result in a non-linear relation between absorption coefficient and film extinction coefficient. Most material other than metals possess, extinction coefficients less than k=0.10. Thus it can be concluded that for non-metallic samples with film thicknesses <400 nm the film surface absorption coefficient will be linear with film extinction coefficient. Hence the film surface absorption of the sample will not be distorted but remains linearly related to the film's extinction coefficient.

Figure 6A:
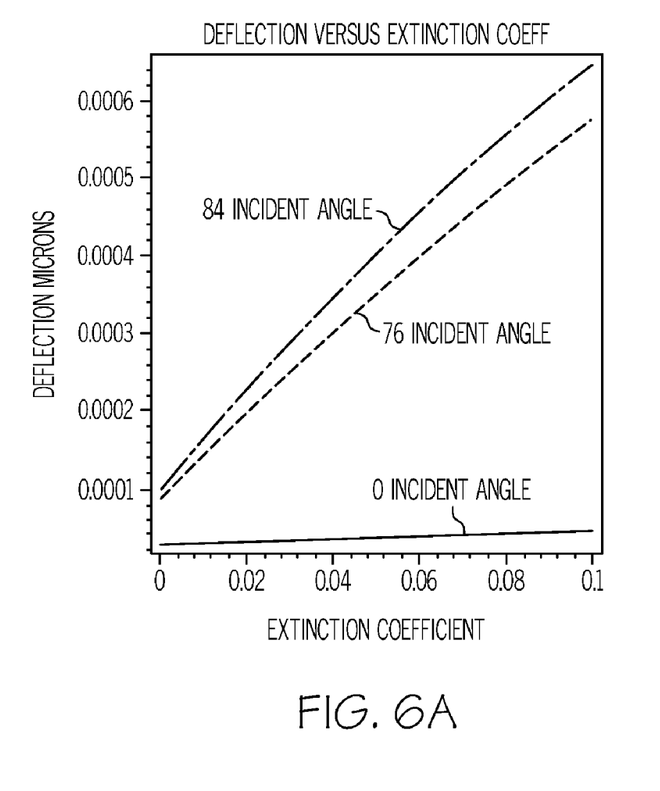
Figure 6B:
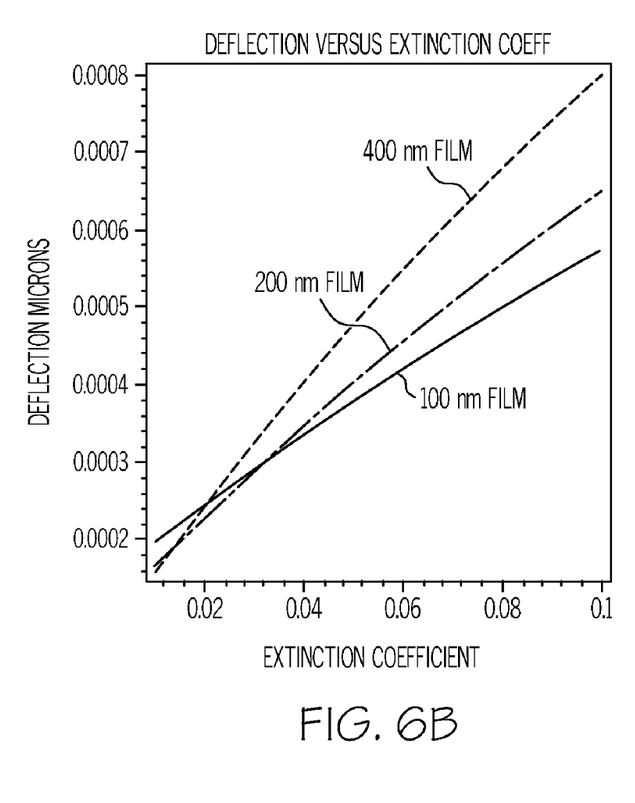

Once the thin film absorption is known and with the incident light Intensity specified, it is possible to calculate the power absorbed by the micro-cantilever. From this and using the thermal and mechanical properties of the bi-material micro-cantilever it is possible to calculate the thermal and mechanical response of the micro-cantilever. A thermal and mechanical model of the bi-material cantilever with a sample film forming the third layer has been constructed. This model can be used to simulate the bending response of the cantilever as a function of power absorbed. FIG. 6 shows the results of these calculations. FIG. 6a shows the calculated cantilever deflection as a function of film extinction coefficient for three incident angles for a 200 nm film. This figure clearly shows the benefit of using grazing incident angle and polarized light. The curve also shows a very linear response by the cantilever as a function of extinction coefficient. FIG. 6b shows the calculated cantilever deflection as a function of film extinction coefficient for three film thicknesses at the optimum grazing incident angles.

Figure 7A:
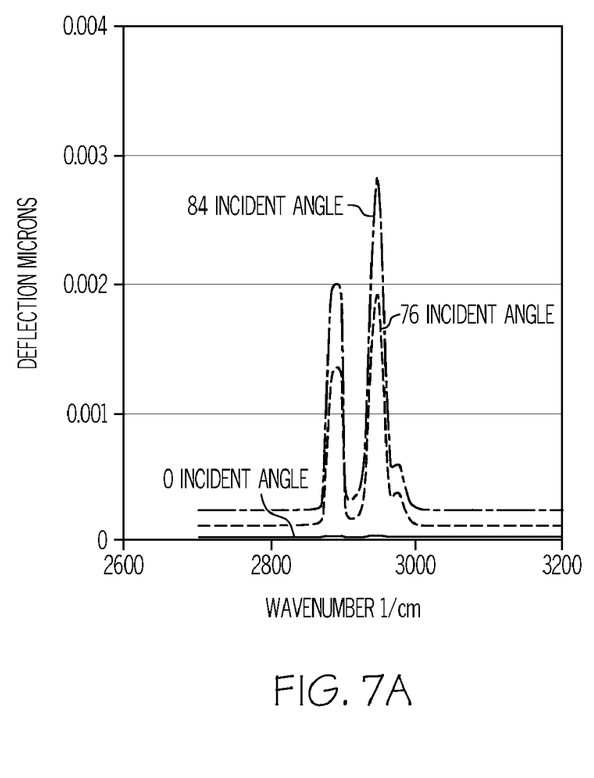
Figure 7B:
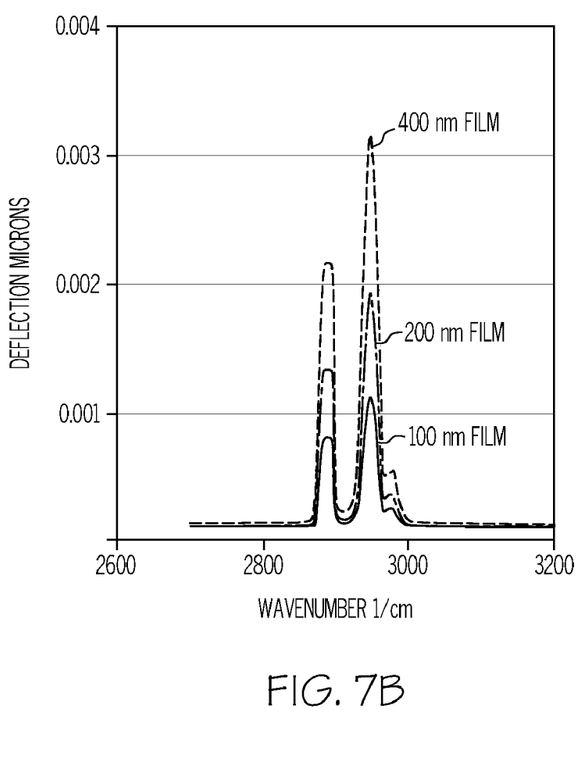

With the cantilever response model incorporating thin film interference effects, and the thermal-mechanical response of the cantilever, it is possible to process Fourier Transform Infrared (FTIR) spectra and compute the expected cantilever response spectra. FIG. 7 shows the results of such a calculation for a C—H bond portion of the polyethylene spectra. FIG. 7 plots cantilever deflection versus wave number from 2600 to 3200 $cm^{-1}$. Examination of this figure also demonstrates the benefits of grazing incident angle polarized IR source. The spectra comparing 0 degree normal incident with that computed for grazing incident clearly shows a factor of 56× improvement in the strength of the cantilever deflection. This gain would result in reducing scan times from 1.5 hours to 1.5 minutes.

The sensor, such as discussed above, can be coupled with an air particle collector and concentrator to collect particles of specific sizes or weights in preparation for distribution and deposition across the one or more micro-cantilever(s) for test and analysis. The sensor can be coupled to collector and concentrator devices that enable the collection of particles from air, water, or solids.

The sensor can be deployed as a network element on a distributed network, or as a stand-alone device, or a hand-held mobile unit.

Described now is an exemplary advanced calorimetric spectrometer system for commercial deployment for applications supporting detection and identification of chemical and/or biological trace materials.

An example of an advanced calorimetric spectrometer sensor system as illustrated in FIG. 2A, provides for detection and identification of chemical and/or biological trace elements by providing consistent and accurate spectral data that can be used to compare at least one photothermal signature against a standard IR spectral database. The inventive features and advantages of various embodiments of an advanced calorimetric spectrometer designed for deployment in commercial applications will be discussed below. However, it is assumed that the reader has an understanding of radiation and sensor technologies.

Figure 8:
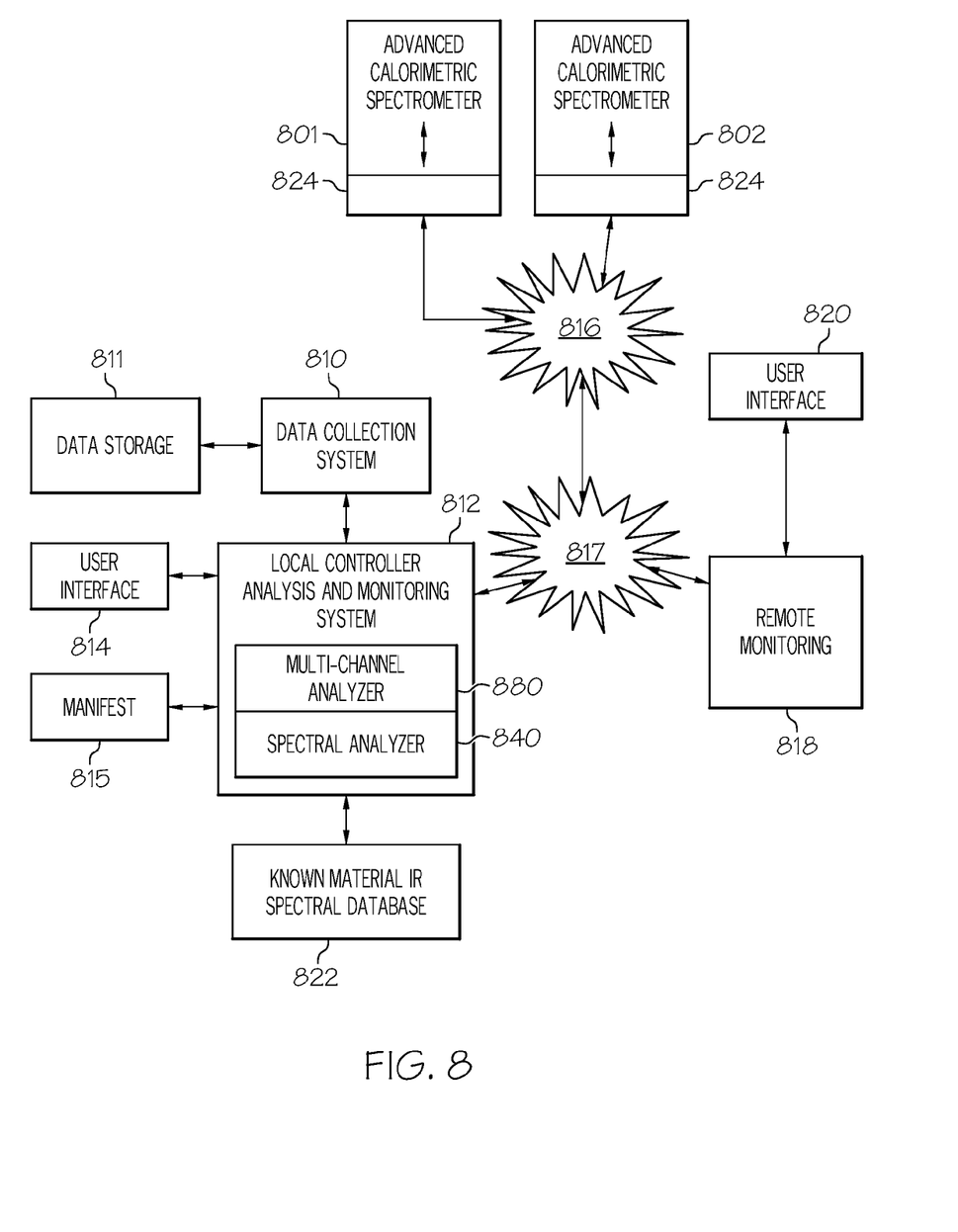
FIG. 8 is a simple schematic illustrating an advanced calorimetric spectrometer system, according to one embodiment of the present invention.

With reference to FIG. 8, a data collection system 810, in this example, is communicatively coupled via cabling, wireless communication link, and/or other communication link or network 816 with each of the advanced calorimetric spectrometer sensor devices in each sensor unit 801, 802. The data collection system 810 includes an information processing system with data storage 811 and with data communication interfaces that collect signals from the sensor units 801, 802, via sensor interfaces 824 at the sensor units 801, 802. The collected signals, in this example, represent detailed spectral data from each sensor device.

The data collection system 810 is modular in design and can be used specifically for chemical and biological material detection and identification, or for data collection for explosives and special materials detection and identification.

The data collection system 810 is communicatively coupled with a local controller and monitor system 812. The local controller and monitor system 812 comprises an information processing system that includes a computer, memory, storage, and a user interface 814 such a display on a monitor and a keyboard, or other user input/output device. In this example, the local system 812 also includes a multi-channel analyzer 880 and a spectral analyzer 840.

The multi-channel analyzer (MCA) 880 comprises a device composed of many single channel analyzers (SCA). The single channel analyzer interrogates analog signals received from the individual micro-cantilever sensor units 801, 802. Heat transfer energy is measured across the provided spectra and a photothermal image accumulated. The photothermal image represents the spectral image of the chemical and/or biological materials that are present.

The photothermal image is used by the spectral analysis system 840 to identify chemical and/or biological materials that are present in materials that are under examination. One of the functions performed by the information processing system 812 is spectral analysis, performed by the spectral analyzer 840, to identify the one or more chemical and/or biological materials contained in the materials under examination. With respect to chemical and/or biological material detection, the spectral analyzer 840 compares one or more spectral images (representing at least one photothermal signature) of the chemical and/or biological materials present to known materials that are represented by one or more spectral images stored in the IR spectra database 822.

By capturing multiple variations of spectral data for each known chemical and/or biological material there are numerous images that can be compared to one or more spectral images of the chemical and/or biological material(s) under examination. The IR spectra database 822 holds the one or more spectral images of each chemical and/or biological material to be identified. These multiple spectral images represent various levels of acquisition of spectral data so chemical and/or biological materials can be compared and identified using various amounts of spectral data available from the one or more sensors 801, 802.

Whether there are small amounts (or large amounts) of data acquired from the sensor(s) 801, 802, the spectral analysis system 840 compares the acquired sensor data from the sensor(s) 801, 802 to one or more spectral images for each chemical and/or biological material to be identified. This significantly enhances the reliability and efficiency of matching acquired spectral image data from the sensor(s) 801, 802, to spectral image data of each possible chemical and/or biological material to be identified. Once the one or more possible chemical and/or biological materials are determined present in the materials detected by the sensor(s) 801, 802, the information processing system 812 can compare the chemical and/or biological mix against possible materials, goods, and/or products, that may be present in the materials under examination.

Additionally, a manifest database 815 includes a detailed description of the contents of a container that is to be examined. The manifest 815 can be referred to by the information processing system 812 to determine whether the possible materials, goods, and/or products, contained in the container match the expected authorized materials, goods, and/or products, described in the manifest for the particular container under examination. This matching process, according to one embodiment of the present invention, is significantly more efficient and reliable than any container contents monitoring process in the past.

The spectral analysis system 840, according to one embodiment, includes an information processing system and software that analyzes the data collected and identifies the chemical and/or biological materials that are present. The spectral analysis software consists of more that one method to provide multi-confirmation of the chemical and/or biological materials identified. Should more than one chemical and/or biological material be present, the system identifies the ratio of each chemical and/or biological material present. Examples of methods that can be used for spectral analysis include: 1) a margin setting method as described in U.S. Pat. No. 6,847,781; and 2) a LINSCAN method (a linear analysis of spectra method) as described in U.S. Provisional Patent Application No. 60/759,331, filed on Jan. 17, 2006, by inventor David L. Frank, and entitled "Method For Determination Of Constituents Present From Radiation Spectra And, If Available, Neutron And Alpha Occurrences"; the collective entire teachings of which being herein incorporated by reference.

The user interface 814 allows service or supervisory personnel to operate the local system 812 and to monitor the status of chemical and/or biological material(s) detection and identification. The user interface 814, for example, can present to a user a representation of the collected data signals, or the identified chemical and/or biological materials determined to be present.

The data collection system 810 and local system 812 can also be communicatively coupled with a remote control and monitoring system 818 such as via a network 817. The remote system 818 comprises an information processing system that has a computer, memory, storage, and a user interface 820 such as a display on a monitor and a keyboard, or other user input/output device. The network 817 comprises any number of communication links, local area networks and/or wide area networks. It can include wired and/or wireless communication networks. This network communication technology is well known in the art. According to one embodiment, the network 817 used for communication between the local controller and monitor system 812 and the remote control and monitoring system 818 can be the same network 816 as used by the data collection system 810 to communicate with each of the advanced calorimetric spectrometer sensor devices in each sensor unit 801, 802. Alternatively, these networks 816, 817 can be two separate networks.

The user interface 820 allows remotely located service or supervisory personnel to operate the local system 812 and to monitor the status of the sensor(s) 801, 802. The remote monitoring system 818 can display an alarm condition, and identify to the service or supervisory personnel the chemical and/or biological materials present at the sensor(s) 801, 802. Additionally, it can display and identify to the service or supervisory personnel whether the sensed possible materials, goods, and/or products, contained in a container under examination matches the declared and authorized content of the container as described in a manifest record for the container, the manifest record being stored in the manifest database 815.

Non-Limiting Examples

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A combined chemical and biological sensor system, comprising:
    at least one micro-cantilever sensing element;
    means for collecting at least one of aerosol, liquid, and solid particles, and depositing by adsorption the particles onto the at least one micro-cantilever and forming a stack including a film layer with the deposited particles on the at least one micro-cantilever sensing element, the deposited particles including one or more chemical or biological species to be analyzed;
    at least one source of plane polarized light adapted to:
        illuminate with plane polarized light the particles on the at least one micro-cantilever sensing element at a grazing incidence angle to a specific wavelength of light, the plane polarized light being polarized substantially in a plane parallel to the stack; and
        radiate and thereby heat the at least one micro-cantilever sensing element with different wavelengths of the plane polarized light spectrum; and
    readout electronics, communicatively coupled with the at least one micro-cantilever sensing element, for detecting movement of the at least one micro-cantilever sensing element as a result of heat transfer to the at least one micro-cantilever sensing element from the light on the stack including the one or more chemical or biological species present, and the readout electronics further for providing photothermal spectral data signals corresponding to the detected movement of the at least one micro-cantilever sensing element;
    a data collection system, communicatively coupled with the readout electronics, for collecting the photothermal spectral data signals from the readout electronics; and
    a spectral analyzer, communicatively coupled with the data collection system, for spectrally analyzing the collected photothermal spectral data signals representing at least one photothermal signature of sensed chemical or biological species, and further for identifying one or more chemical or biological species present.

2. The system of claim 1, wherein the spectral analyzer is further adapted to:
    prepare spectral images of the collected photothermal spectral data signals, the spectral images representing the at least one photothermal signature; and
    compare the spectral images representing the at least one photothermal signature with one or more spectral images of possible chemical or biological species to find a match and thereby to identify one or more chemical or biological species present.

3. The system of claim 2, further comprising:
    a spectral database for storing one or more spectral images representing one or more known chemical or biological materials, the spectral analyzer being communicatively coupled with the spectral database for comparing the spectral images representing the at least one photothermal signature with the stored one or more spectral images representing one or more known chemical or biological materials to find a match.

4. The system of claim 3, wherein the stored one or more spectral images represent various levels of acquisition of spectral data associated with known chemical and biological materials for comparing the spectral images representing the at least one photothermal signature with the one or more spectral images representing various levels of acquisition of spectral data associated with known chemical and biological materials to identify the one or more chemical or biological species present by using various amounts of spectral data available from the at least one micro-cantilever sensing element.

5. The system of claim 2, further comprising:
a manifest database including detailed description of a content of a container that is to be examined; and
an information processing system, communicatively coupled with the spectral analyzer and the manifest database, for matching identified one or more chemical or biological species present to possible materials, goods, and/or products, contained in the container, and to determine whether the possible materials, goods, and/or products, contained in the container match expected authorized materials, goods, and/or products, described in a manifest record stored in the manifest database for the container under examination.

6. The system of claim 1, wherein the at least one micro-cantilever sensing element comprises at least one of:
a single test element,
a one dimensional array of micro-cantilevers, and
a two dimensional array of micro-cantilevers.

7. The system of claim 1, wherein the at least one source of plane polarized light illuminates the particles on the at least one micro-cantilever sensing element at a grazing incidence angle in a range of between approximately 70 degrees and 80 degrees.

8. The system of claim 1, wherein the light is IR light polarized substantially in a plane parallel to a surface of the film layer deposited by adsorption on the at least one micro-cantilever sensing element.

9. The system of claim 1, wherein the at least one micro-cantilever sensing element comprises a thermal detector.

10. The system of claim 1, wherein the at least one micro-cantilever sensing element comprises a balometer array.

11. The system of claim 1, wherein the at least one micro-cantilever sensing element comprises a thermopile array.

12. The system of claim 1, wherein the at least one source of plane polarized light comprises a plurality of sources of plane polarized light.

13. The system of claim 12, wherein the at least one source of plane polarized light comprises a plurality of sources of IR light.

14. The system of claim 12, wherein the at least one source of plane polarized light comprises:
a plurality of sources of IR light;
collimating optics for each of the sources of IR light to provide polarized IR light; and
a beam combiner to combine the polarized IR light from the plurality of sources of IR light.

15. The system of claim 12, wherein the at least one source of plane polarized light comprises:
a parabolic mirror to reflect the plane polarized light from the at least one source and aim the plane polarized IR light at a grazing incidence angle to the at least one micro-cantilever sensing element.

16. A method for sensing chemical and biological materials, the method comprising:
collecting particles from an aerosol, liquid, or solids including one or more chemical or biological species to be analyzed;
depositing the collected particles on at least one micro-cantilever sensing element forming a stack including a film layer with the deposited particles on the at least one micro-cantilever sensing element;
illuminating with plane polarized light the particles on the at least one micro-cantilever sensing element at a grazing incidence angle to a specific wavelength of light, the illuminating light being polarized substantially in a plane parallel to the stack;
heating the at least one micro-cantilever sensing element by radiating the at least one micro-cantilever sensing element with different wavelengths of the plane polarized IR light provided at a grazing incidence to a specific wavelength; and
detecting movement of the at least one micro-cantilever sensing element as a result of heat transfer to the at least one micro-cantilever sensing element from the illuminating light on the stack;
providing a photothermal signature of a sensed chemical or biological material corresponding to the detected movement of the at least one micro-cantilever sensing element; and
spectrally analyzing the photothermal signature of sensed chemical or biological species present.

17. The method of claim 16, wherein the spectrally analyzing comprises:
comparing the photothermal signature with one or more spectral images of possible chemical or biological species present.

18. The method of claim 16, wherein the spectrally analyzing comprises:
comparing one or more spectral images representing the photothermal signature with one or more spectral images of possible chemical or biological species present; and
determining whether the one or more spectral images representing the photothermal signature match the one or more spectral images of possible chemical or biological species present that identify the sensed chemical or biological species present.

19. The method of claim 16, wherein the illuminating with plane polarized light consists of illuminating with plane polarized IR light from a plurality of sources of IR light.

20. The method of claim 16, wherein the illuminating with plane polarized light comprises illuminating with plane polarized IR light at a grazing incidence angle in a range of between approximately 70 degrees and 80 degrees.

* * * * *